United States Patent
Pacetti et al.

(10) Patent No.: US 7,955,615 B2
(45) Date of Patent: *Jun. 7, 2011

(54) POLYCATIONIC PEPTIDE COATINGS AND METHODS OF COATING IMPLANTABLE MEDICAL DEVICES

(75) Inventors: Stephen D. Pacetti, San Jose, CA (US); Eugene T. Michal, San Francisco, CA (US); Syed F. A. Hossainy, Fremont, CA (US); Ni Ding, San Jose, CA (US); Wouter E. Roorda, Palo Alto, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 1229 days.

This patent is subject to a terminal disclaimer.

(21) Appl. No.: 11/212,376

(22) Filed: Aug. 26, 2005

(65) Prior Publication Data

US 2006/0002974 A1    Jan. 5, 2006

Related U.S. Application Data

(62) Division of application No. 10/177,116, filed on Jun. 21, 2002, now Pat. No. 7,033,602.

(51) Int. Cl.
*A61F 2/04* (2006.01)
(52) U.S. Cl. ........................................ 424/424
(58) Field of Classification Search .................. None
See application file for complete search history.

(56) References Cited

U.S. PATENT DOCUMENTS 7,011,842 B1    3/2006  Simhambhatta et al.
7,033,602 B1 *  4/2006  Pacetti et al. ............ 424/426

* cited by examiner

*Primary Examiner* — Carlos A Azpuru
(74) *Attorney, Agent, or Firm* — Squire, Sanders & Dempsey (US) LLP

(57) ABSTRACT

Coatings for medical devices which include polycationic peptides such as L-arginine and methods for fabricating the coatings are disclosed.

8 Claims, No Drawings

POLYCATIONIC PEPTIDE COATINGS AND METHODS OF COATING IMPLANTABLE MEDICAL DEVICES

CROSS REFERENCE

This application is a divisional of application Ser. No. 10/177,116, filed Jun. 21, 2002 now U.S. Pat. No. 7,033,602, which is hereby incorporated herein by reference.

BACKGROUND OF THE INVENTION

1. Field of the Invention

This invention relates to the field of medical devices, such as stents. More particularly, this invention is directed to coatings which include polycationic peptides such as polymers and/or oligomers of L-arginine.

2. Description of the State of the Art

In the field of medical technology, there is frequently a necessity to administer a therapeutic substance locally. To provide an efficacious concentration to the treatment site, systemic administration of medication often produces adverse or toxic side effect for the patient. Local delivery is a preferred method in that smaller total levels of medication are administered in comparison to systemic dosages, but are concentrated at a specific site. Thus, local delivery produces fewer side effects and achieves more effective results. For the treatment of vascular occlusions, such as restenosis, stents are being modified to administer therapeutic substances locally. One method of medicating a stent is with the use of a polymer coating impregnated with a therapeutic substance. The coating allows for the sustained release of the substance at the treatment site. L-arginine, or polypeptide oligomeric derivatives or analogs thereof, for example, those containing 5 to 20 amino acid units are one example of a therapeutic substance that can be used in conjunction with a stent.

L-arginine is a known precursor of endothelium derived nitric oxide (NO). NO is synthesized from L-arginine, or its polymeric and/or oligomeric derivatives, by the enzyme NO synthase oxygenase, a homodimeric flavo-hemoprotein that catalyzes the 5-electron oxidation of L-arginine to produce NO and L-citrulline. Among other therapeutic properties, NO regulates vascular tone, inhibits platelet aggregation, and inhibits vascular smooth muscle proliferation. These therapeutic properties are believed to contribute to the reduction or elimination of neo-intimal hyperplasia in vascular injury models.

U.S. Pat. No. 5,861,168 to Cooke et al. teaches that NO activity is reduced after vascular injury. Cooke et al. also teach that administering L-arginine as the NO precursor helps to restore vascular NO activity in patients with endothelial vasodilator dysfunction due to restenosis. It has been also taught that oligomeric peptides comprising 6 to 15 units of L- or D-arginine can be effective transfectors of cells (see, Mitchell, et al., *J. Peptide Res.*, vol. 56, p. 318 (2000)) and, using a rabbit vein-graft model, it has been demonstrated that oligomers of L- or D-arginine can inhibit vascular smooth cell proliferation by efficiently transfecting cells. See, Uemura, et al., *Circulation*, vol. 102, p. 2629 (2000). Using the rabbit model, it has also been shown that intramural administration of L-arginine inhibits lesion formation in a hypercholesterolemic balloon injury. See, Schwarzacher et al. *Circulation*, vol. 95, p. 1863 (1997).

Due to the strong basicity of the guanidinium group, —NH—C(NH$_2$)=NH, L-arginine is highly cationic. For example, the heptamer of L-arginine has the pK$_a$=13.2. This high degree of polarity causes L-arginine, or its polymers and/or oligomers, to be practically insoluble in most organic solvents having the Hildebrand solubility parameter $\delta \leq 12.7$ (cal/cm$^3$)$^{1/2}$.

The term "Hildebrand solubility parameter" refers to a parameter measuring the cohesion of a substance. The $\delta$ parameter is determined as follows:

$$\delta = (\Delta E/V)^{1/2}$$

where $\delta$=solubility parameter, (cal/cm$^3$)$^{1/2}$;
$\Delta E$=energy of vaporization, cal;
V=molar volume, cm$^3$ The more polar the solvent, the higher its cohesion due to the existence of strong van der Waals forces. Consequently, it takes more energy to vaporize more polar substances, resulting in the higher numerical value of $\delta$.

Thus, L-arginine or its polymers and/or oligomers are believed to be soluble only in water ($\delta$=23.4 (cal/cm$^3$)$^{1/2}$)(as much as 15% by weight concentration in water can be achieved for the heptamer of L-arginine) and have some limited solubility only in very polar solvents having high values of $\delta$, for example, formamide ($\delta$=19.2 (cal/cm$^3$)$^{1/2}$), methanol ($\delta$=14.5(cal/cm$^3$)$^{1/2}$), or ethanol ($\delta$=12.7 (cal/cm$^3$)$^{1/2}$).

While polycationic peptides, such as L-arginine, are practically insoluble in many organic solvents, the polymers from which the stent coatings are made are soluble in organic solvents but not water. The incompatibility of solubility of the polymer and L-arginine in a common solvent or common mixture of solvents can lead to poor coating characteristics and poor release profile of the peptide from the coating. Furthermore, the high degree of solubility of polycationic peptides in water tends to increase the in vivo rate of release of the peptides, which may be undesirable. Polycationic peptides are essentially incompatible with hydrophobic polymers which are commonly used to coat a stent. The embodiments of the present invention address these and other deficiencies.

SUMMARY

The embodiments of the present invention generally encompass the field of medical devices, wherein the medical device can comprise a stent. More particularly, this invention is directed to coatings which include polycationic peptides such as polymers and/or oligomers of L-arginine, such as hepta-arginine.

In some embodiments the invention includes a coating for an implantable medical device, wherein the coating comprises a polymer and a complex comprising a polycationic peptide and a counter-ion, wherein the complex is bonded to the polymer. In some embodiments, the invention includes a method of coating an implantable medical device comprising applying a polymer composition onto a medical device and bonding an anionic polysaccharide-peptide complex to the polymer.

In some embodiments, the invention includes a method of coating an implantable medical device with a polymer composition comprising a polycationic peptide, wherein the method comprises applying onto the device an organic solvent solution comprising a polymer and a complex of the peptide with a hydrophobic counter-ion to form the coating and heat-treating the coating.

In some embodiments, the invention includes a method of delivering an agent to a mammalian tissue, wherein the method comprises contacting the coatings of the present invention with mammalian tissue under in vivo conditions. In these embodiments, the tissue can comprise a vascular tissue.

In some embodiments, the invention includes a method of preventing or treating a disease comprising implanting the coatings of the present invention in a vascular lumen. In these embodiments, the disease can include a vascular disease comprising restenosis, vulnerable plaque, or a combination thereof, and the implanting can include the placement of a stent.

DETAILED DESCRIPTION

L-arginine, also known as 2-amino-5-guanidinovaleric acid, is an amino acid having a formula $NH=C(NH_2)-NH-CH_2-CH_2-CH_2-CH(NH_2)-COOH$. Polymers and/or oligomers of L-arginine that can be used are referred to herein as "PArg" and comprise a plurality of repeating monomeric amino acid units connected with peptide bonds. PArg has a general formula $H[NH-CHX-CO]_p-OH$, where "p" can be within a range of 5 and 1,000, typically, within a range of between 6 and 20. For example, a heptamer (designated R7), having p=7, can be used.

In the formula of PArg, "X" is a 1-guanidinopropyl radical having the chemical structure $-CH_2-CH_2-CH_2-NH-C(NH_2)=NH$. The terms "polymers and/or oligomers of L-arginine," "poly-L-arginine," and "PArg" are intended to include L-arginine in both its polymeric and oligomeric form. Representative examples of these polycationic peptides include poly(L-arginine), poly(D-arginine), poly(D,L-arginine), poly(L-lysine), poly(D-lysine), poly(δ-guanidino-α-aminobutyric acid), racemic mixtures of poly(L-arginine) and poly(D-arginine), and chitosan.

A. Achieving Solubility of PArg in Organic Solvents by Coordinating PArg with Hydrophobic Counter-Ions In one embodiment for achieving solubility of PArg in an organic solvent, PArg is coordinated with hydrophobic counter-ions. The hydrophobic counter-ions with which PArg and other suitable polypeptides can be coordinated include anions $Z-COO^-$ of the following saturated fatty acids $Z-COOH$: formic ($Z=H$), acetic ($Z=CH_3$), propionic ($Z=C_2H_5$), butyric ($Z=C_3H_7$), valeric ($Z=C_4H_9$), caproic ($Z=C_5H_{11}$), enanthic ($Z=C_6H_{13}$), caprylic ($Z=C_7H_{15}$) pelargonic ($Z=C_8H_{17}$), capric ($Z=C_9H_{19}$), hendecanoic ($Z=C_{10}H_{21}$), lauric ($Z=C_{11}H_{23}$), myristic ($Z=C_{13}H_{27}$), palmitic ($Z=C_{15}H_{31}$), stearic ($Z=C_{17}H_{35}$), and arachidic ($Z=C_{19}H_{39}$). The anions can be derived from the acids themselves or from their salts, for example, from sodium salts $ZCOO^-Na^+$.

The hydrophobic counter-ions with which PArg and other suitable polypeptides can be coordinated also include anions $Z'-COO^-$ of the following unsaturated fatty acids $Z'-COOH$: palmitoleic ($Z'=C_{15}H_{29}$), oleic ($Z'=C_{17}H_{33}$), linoleic ($Z'=C_{17}H_{31}$), arachidonic ($Z'=C_{19}H_{31}$), or from salts thereof, for example, from sodium salts $Z'COO^-Na^+$.

Other compounds that can be used to generate acceptable hydrophobic counter-ions with which PArg and other suitable polypeptides can be coordinated include phoshpolipids, for example, phosphatidic acids, phosphatidylinositol, phosphatidylglycerol, diphosphatidylglycerol, or salts thereof; sulfates, for example, sodium dodecyl sulfate; and aromatic compounds, for example, benzoic acid, salicylic acid, acetyl salicylic acid (known as aspirin) and aromatic sulfonates, and anionic biologically active compounds. Examples of such suitable hydrophobic anionic biologically active compounds include statins, retinoic acid and retinoids. The hydrophobic counter-ions that can be used are herein designated as $AN^-$.

PArg such as R7 is commonly produced by peptide synthesis. The synthesis is known to those having ordinary skill in the art. At the end of the peptide synthesis, R7 is cleaved off the support resin, usually with trifluoroacetic acid (TFA) or trifluoromethane sulfonic acid. The hydrophobic counter-ion, such as one of the counter-ions $AN^-$ described above, is then coordinated with R7 using one of the following methods.

1. Free Base Method.

The free base method is directed to formation of the free base of R7. R7 can be dissolved in water and a strong alkali can be added, such as potassium hydroxide KOH, so as to create a homogeneous basic solution. The pH of the R7 solution (solution I) in water can be typically raised to about 13. In such a strongly alkaline environment, the guanidinium side branches of R7 are de-protonated and R7 in a free base form can be obtained as a result. In the free base form, R7 has only one charged group, an anionic carboxyl at one terminus. The guanidinium side groups are neutral. For the purposes of this invention, R7 in the free base form is designated as R7-FB.

One of the above-identified substances forming hydrophobic counter-ions $AN^-$, or a mixture of such substances, can be dissolved in an appropriate organic solvent, such as toluene, methylene chloride, octanol, cyclohexane, chloroform, or diethyl ether (solution II). R7-FB obtained as described above can then be extracted into solution II by blending and vigorously shaking the free base aqueous solution I and solution II.

As a result of the extraction, R7-FB will migrate into the organic solution. The hydrophobic counter-ions in the form of the free acid will also remain in the organic phase. If a stoichiometric amount of KOH is used to make the R7-FB, the R7-FB will both migrate into the organic phase and undergo an acid-base reaction forming a $R7+/AN^-$ complex that is soluble in the organic phase. After separating the organic phase from the aqueous phase, the complex can then be isolated from the organic phase by evaporating the solvent, cooling the solution, or precipitating by a compound which is a non-solvent for the complex.

2. Dialysis Method.

According to this method, an aqueous solution of $R7^+$ in the free base form can be made as described above. The R7 solution can be dialyzed using standard techniques known to those having ordinary skill in the art. Typically, a dialysis membrane having a molecular weight cut-off of about 1,000 can be used for the R7 solution. The purpose of the dialysis is to remove the counter-ions that were originally with R7, such as trifluoro acetate. If desired, the progress of the dialysis can be monitored by measuring the conductivity of the R7 solution.

Once the aqueous solution of $R7^+$ in the free base form is purified to a degree of purity to be determined by those having ordinary skill in the art, the solution can be brought into contact with a solution of one, or a mixture of more than one, $AN^-$ in an acid form, in an appropriate organic solvent, such as methyl ethyl ketone, methylene chloride, toluene, chloroform, or diethyl ether.

As a result, R7-FB will undergo an acid-base reaction with the free acid counter-ion and a $R7+/AN^-$ complex will accumulate in the organic phase.

3. Ion Exchange Method.

The R7-based complex containing a water soluble counter-ion, for example, fluoride-ion or chloride ion, can be prepared. The complex ($R7+/F^-$) can be made, for example, by conventional cleavage and de-protection steps in peptide synthesis. It can also be made by adding an appropriate acid (e.g., HF, or HCl) to an aqueous solution of R7 free base. Those having ordinary skill in the art can select the R7:acid ratio to be employed.

A solution of one of the substances forming hydrophobic counter-ions or a mixture of more than one of such substances, for example, lithium, or sodium laurate ($C_{11}H_{23}COOMe^+$), or lauric acid, can be prepared in an appropriate organic solvent, such as chloroform, diethyl ether, toluene, or cyclohexane. In the formula of the laurate above, $Me^+$ is an alkali metal cation.

The aqueous solution of $R7^+/F^-$ complex can then be mixed with the organic solution of $C_{11}H_{23}COOLi^+$. Since $F^-$ and $Li^+$ prefer to be in the aqueous phase (due to their large heats of salvation), and the $R7^+$ cation and the laurate anion $C_{11}H_{23}COO^-$ are soluble in the organic phase, the corresponding "swap" or exchange of ions takes place. As a result, $R7^+$ having the hydrophobic counter-ion $C_{11}H_{23}COO^-$ coordinated to $R7^+$, accumulates in the organic phase and becomes organic solvent soluble, while the $Li^+F^-$ salt accumulates in the aqueous phase.

Alternatively, the ion "swap" can be performed in an ion exchange column. According to this embodiment, the aqueous solution of R7 can be run through an ion exchange column containing an anion exchange resin, the column to be selected according to standard criteria known to those having ordinary skill in the art. An example of suitable anion exchange resin can be a phenolic resin with quaternized hydrophobic amino substituents. Other example of a suitable anion exchange resin can be a resin which includes $AN^-$ coordinated against the quaternized amino substituents. Such alternative anion exchange resin can be dissolved in a mixed alcohol-water solvent or a strong solvent, for example, dimethylsulfoxide.

If the anion exchange column is loaded with $AN^-$, emerging from the column will be the R7 coordinated with the $AN^-$ hydrophobic counter-ion. If the ion exchange column is loaded with hydroxide anion, $OH^-$, then this ion will swap for the counter-ion being present, for example the anion of trifluoroacetic acid. The R7 free base emerging from the column can then be contacted with an organic phase containing the organic acid and the organo-soluble $R7^+/AN^-$ complex will form.

4. The Method of Selective Precipitation.

According to this method, the aqueous solution of $R7^+/Cl^-$ complex can be prepared as described above. A solution of one of the substances forming hydrophobic counter-ions, for example, potassium laurate in an appropriate organic solvent can be prepared, as described above. The two solutions can be brought into a contact and silver hydroxide or silver oxide can be slowly added. Silver chloride, AgCl, will precipitate due to its extremely low solubility driving R7 into the organic phase where it will be coordinate with the $AN^-$ (the laurate anion) forming an organo-soluble $R7^+/AN^-$ complex, in this case, $R7^+$/laurate complex.

5. The Method of Volatilization of Counter-Ions.

According to this method, the aqueous solution of $R7^+/AN^-$ complex can be prepared. The $AN^-$ here is the anion of a volatile organic acid. One example of such a volatile organic acid is acetic acid, and $AN^-$ is accordingly the acetate-anion. A solution of the desired free acid, to ultimately become the hydrophobic counter-ion, for example, lauric acid, is prepared in an appropriate water-immiscible organic solvent. The two solutions can then be brought into contact and heated to a temperature sufficient to cause evaporation of the acetic acid, for example, about 100 deg. C. As acetic acid evaporates, it will drive the R7 into the organic phase to coordinate with the laurate ion.

The organo-soluble $R7^+/AN^-$ complex obtained by any method described above can be incorporated into a polymer layer coated on an implantable device, such as a stent. By way of example, the $R7^+/AN^-$ complex and a polymer forming a layer on a device can be dissolved in an organic solvent and the solution containing both the polymer and the $R7^+/AN^-$ complex can be applied by spraying or dipping techniques.

One variation of a method of volatilization of counter-ions can be used for facilitating the process of incorporating R7 into some polymer compositions. For example, it would be beneficial to blend R7 into an acrylic composition, then to apply the blend onto the stent. However, in the case of acrylic compositions which include carboxyl groups, such blending is often not feasible. For example, if the polymer contains units derived from acrylic acid, the composition is available in aqueous dispersion. When R7 is added to the dispersion, the stability of the dispersion is disturbed leading to coagulation.

The problem of coagulation can be overcome if R7 is used as a $R7^+/AN^-$ complex. One example of a suitable $R7^+/AN^-$ complex includes an acetate counter-ion $AN^-$. The $R7^+$/acetate complex can be prepared as described above. The complex is organo-soluble and a solution of $R7^+$/acetate complex in dimethylacetamide can be prepared, the solution containing between about 1% and about 10% by mass of $R7^+$/acetate complex.

The solution of $R7^+$/acetate complex can then be combined with a solution of poly(butylmethacrylate-co-acrylic acid) in a 70:30 (mass) mixture of dimethylacetamide and ethanol, the solution having between about 3% and about 5% (mass) of poly(butylmethacrylate-co-acrylic acid). The blend of the solutions of $R7^+$/acetate complex and of poly(butylmethacrylate-co-acrylic acid) can then be applied onto a stent as a "drug-polymer layer," and/or as a "topcoat layer," for example by spraying, to form a coating containing $R7^+$/acetate complex dispersed in poly(butylmethacrylate-co-acrylic acid).

This coating is then heated at a temperature of about 100° C. for about 2 hours leading to removal of acetic acid by volatilization and leaving R7 incorporated into poly(butylmethacrylate-co-acrylic acid). Ratios between the solutions of $R7^+$/acetate complex and of poly(butylmethacrylate-co-acrylic acid) are selected so as to have the ratio between R7 and poly(butylmethacrylate-co-acrylic acid) in the final coating between about 1:1 and 1:5, for example, 1:2.

Alternatively, a counter-ion $AN^-$ other than acetate can be used, as long as it can be volatilized at relatively low temperatures. One example of such suitable counter-ion is formate-anion $HCOO^-$ derived from formic acid HCOOH. Besides poly(butylmethacrylate-co-acrylic acid), other acrylic acid-containing polymers can be used, such as poly(ethylene-co-acrylic acid) (PEAA) having a general formula $-[CH_2-CH_2]_r-[CH_2-CH(COOH)]_s-$, where "r" and "s" are integers. PEAA is commercially distributed under a trade name PRIMACOR and can be obtained from Dow Plastics Co. of Midland, Mich. Other alternative suitable polymers include copolymers of maleic, methacrylic or itaconic acid with ethylene, other olefins, or other unsaturated monomers, for example, copolymers of acrylate esters, styrene and acrylic or methacrylic acid in a form of aqueous acrylic dispersion resins known under the trade name CARBOSET available from Goodrich Corp. of Charlotte, N.C.

B. Incoroporating PArg Into Stent Coatings Through the Entrapment of PArg on the Coating' Surface PArg such as R7 can be entrapped on the stent by one of the following methods:
(1) covalent conjugation of R7 to the polymer of the outermost layer of the stent coating;
(2) ionic coordination of R7 to the polymer coating on the stent; and
(3) "reversed" covalent conjugation.

After R7 has been entrapped by one of these methods, it can be coordinated with a counter-ion supplied by a polysaccharide or a combination of polysaccharides.

1. Covalent Conjugation of R7.

One method of incorporating PArg, such as R7, into the coating is by covalent attachment of the peptide to a functionalized surface of the coating followed by formation of an R7/polysaccharide complex. To covalently attach R7 to a stent, the stent can be coated with a polymer coating where the polymer of outermost layer of the coating, such as the reservoir layer or the optional topcoat layer, contains reactive groups, for example hydroxyl, glycidyl, amino, carboxyl, and/or other reactive groups, or a combination thereof. R7 can be chemically bonded to the polymer's backbone utilizing one or more of the pendant reactive groups.

A copolymer of ethylene and vinyl alcohol (EVOH) is one example of a polymer to which R7 can be chemically grafted. Poly(ethylene-co-vinyl alcohol) is also known under the trade name EVAL and is distributed commercially by Aldrich Chemical Company of Milwaukee, Wis. EVAL is also manufactured by EVAL Company of America of Lisle, Ill. EVAL has the general formula $—[CH_2—CH_2]_m—[CH_2—CH(OH)]_n—$, where m and n are integers. EVAL is a product of hydrolysis of ethylene-vinyl acetate copolymers. Those having ordinary skill in the art of polymer chemistry will understand that EVAL may also be a terpolymer and may include up to 5% (molar) of units derived from styrene, propylene and other suitable unsaturated monomers.

Representative examples of other suitable polymers that can be used to fabricate a coating to which PArg (e.g., R7) can be chemically bonded include poly(butylmethacrylate-co-2-hydroxyethyl methacrylate), PBMA-PHEMA, poly(butylmethacrylate-co-acrylic acid), PBMA-PAA, poly(ethylene glycol) (PEG), EVAL-PEG blends, poly(ethylene-co-glycidyl methacrylate) (PEGMA), poly(ethyleneimine)(PEI), poly(ethylene-co-acrylic acid) (PEAA), and other copolymers having units derived from acrylic acid. The grafting of PArg to the polymer can be conducted directly on the stent or the grafting to the polymer can be achieved first, and the product of grafting is then applied on the stent.

Grafting R7 to EVAL is accomplished by esterification. First, EVAL can be halogenated by phosphorous trichloride $PCl_3$, phosphorous pentachloride $PCl_5$, thionyl chloride $SOCl_2$, or other appropriate halogenating agent, via EVAL's hydroxyl group. This process, a nucleophilic substitution $S_N2$ can be schematically illustrated according to reaction (I):

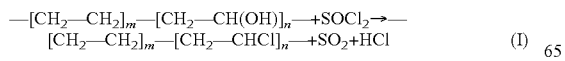

(I)

The non-protonated non-terminal primary amino groups of R7 are protected by reaction (II) with 9-fluorenylmethyl chloroformate in aqueous dioxane as shown below. The 9-fluorenylmethyl chloroformate, also known as 9-fluorenylmethyloxycarbonylchloride or FMOC-chloride, has the formula

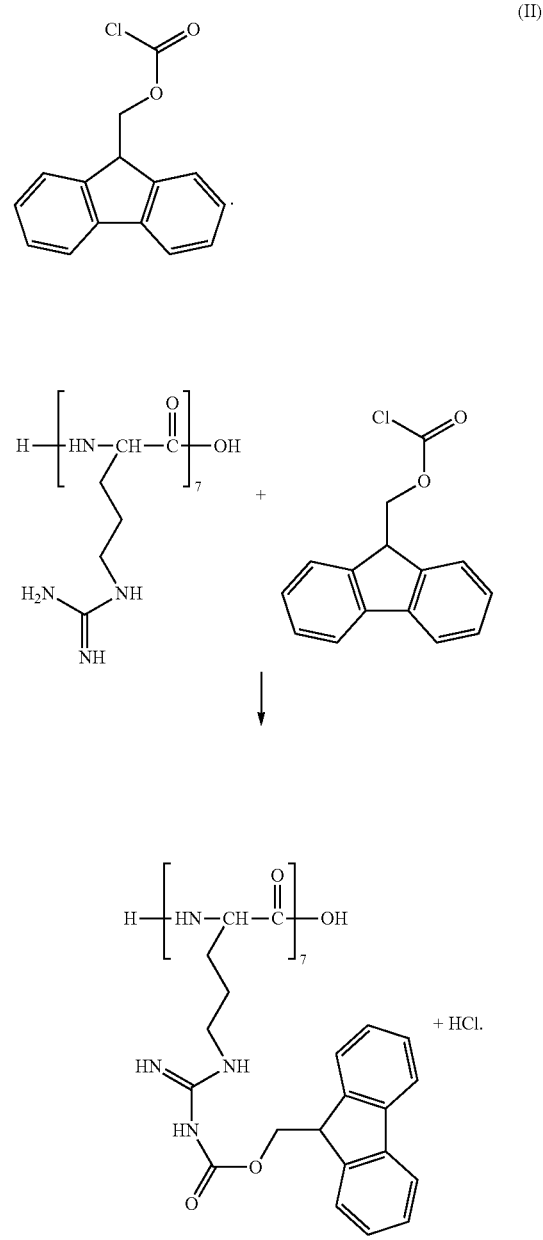

Alternatively, the amino groups of R7 can be protected using tBOC (di-tert-butyl dicarbonate) instead of FMOC. Next, the reaction of esterification is carried as illustrated by reaction (III). In the reaction of esterification, the carboxyl group of the protected molecule of R7 is reacted with the halogenated EVAL obtained in reaction (I):

(III)

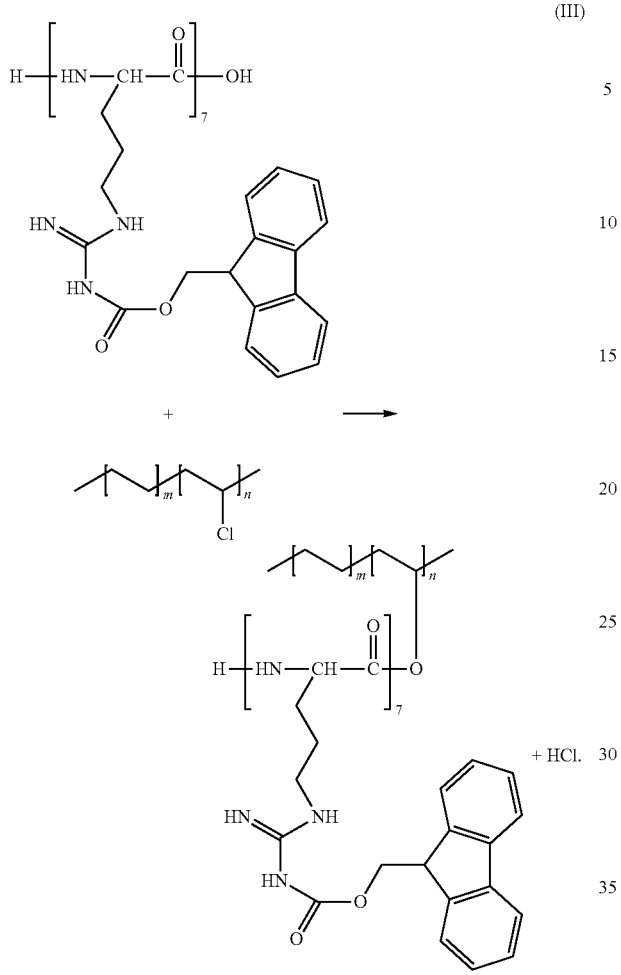

+ HCl.

Finally, the product of reaction III is cleaved by 50% morpholine or other appropriate amine. As a result, the 9-fluorenylmethyl group is removed and R7 is tethered to EVAL by the ester bond, as shown by formula (IV):

(IV)

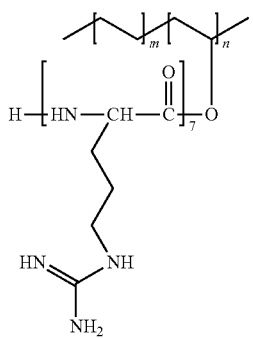

The reactions described above are conducted under the standard conditions which are known to those having ordinary skill in the art.

Alternatively, the protected R7 can be conjugated to EVAL by the reaction of direct esterification, which can be carried out in the presence of 1,3-dicyclohexylcarbodiimide (DCC). DCC activates the carboxyl group of R7, thus facilitating the esterification reaction of nucleophilic substitution (V):

(V)

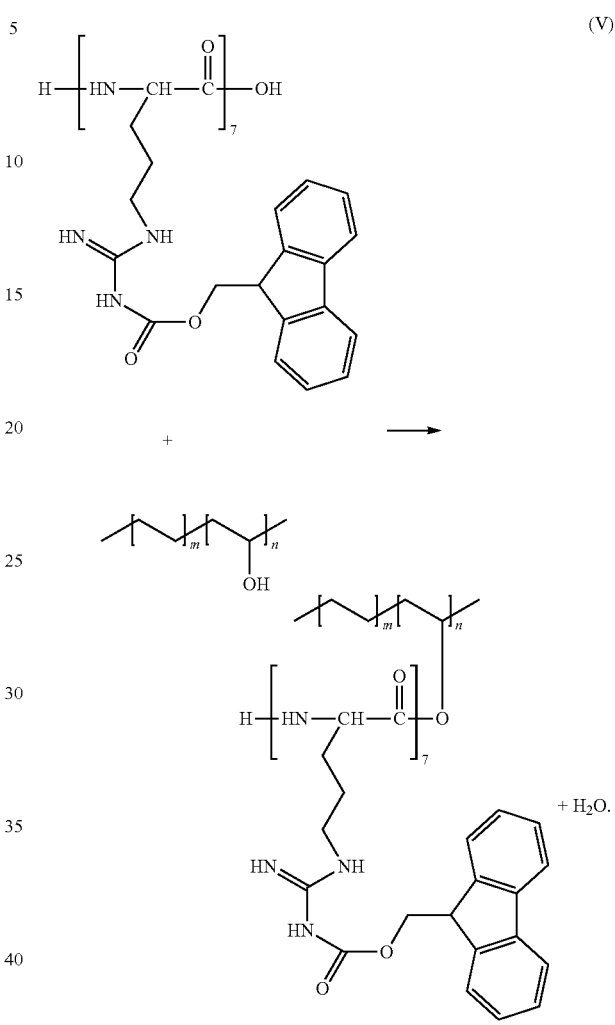

+ H₂O.

Reaction (V) is conducted under standard conditions known to those having ordinary skill in the art. An insoluble substance, N,N-dicyclohexylurea having the formula

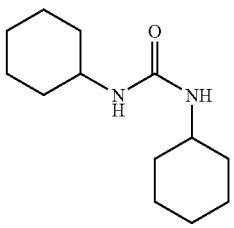

is a by-product of the reaction (V). Finally, the R7-EVAL conjugate, the product of reaction (V), is de-protected by the same reaction with morpholine or another appropriate amine.

In accordance with yet another embodiment, the reaction of direct esterification can be carried out in the presence of dimethylaminopyridine (DMAP).

Due to the presence of a very strongly basic guanidinium fragment and of the acidic carboxyl group, R7, in the non-conjugated to EVAL form, is a zwitterion—a substance having dual acid-base nature. When R7 is esterified, the hydroxyl fragment of the carboxyl group (and the negative charge it carries) is removed. As a result, the R7-EVAL conjugate is a cation. This cation is designated as POL-R7$^+$, where POL is a polymer to which R7 is conjugated, in this case, EVAL. The positive'charge is mainly concentrated on the imino nitrogen of R7 (NH=fragments).

After the POL-R7$^+$ cation is formed, it can be brought into contact with a naturally occurring anionic polysaccharide, or a blend thereof. One appropriate polysaccharide is heparin or a derivative thereof (Hep$^-$) such as heparin salts and heparinoids. Examples of other suitable anionic polysaccharides include dermatan sulfate, keratan sulfate, chondroitin sulfate, hyaluronic acid and hyaluronates. The Hep$^-$ coordinates around POL-R7$^+$, thus entrapping R7 on the stent surface by forming a complex POL-R7$^+$/Hep$^-$ as shown by reaction (VI):

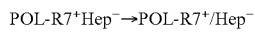

POL-R7$^+$Hep$^-$→POL-R7$^+$/Hep$^-$      (VI)

According to another embodiment, R7 can be grafted to a surface containing amino groups, for example, when the outermost layer of the stent coating includes PEI. PEI has a general formula $NH_2—[CH_2—CH_2—N(CH_2—CH_2—NH_2)]_p—[CH_2—CH_2—NH]_q—$, where "p" and "q" are integers. PEI is commercially manufactured and can be obtained from Economy Products Co. of Houston, Tex.

In order to graft R7 to PEI, the primary amino groups of R7 are first protected by FMOC or tBOC, as shown by reaction II. Next, the protected R7 is reacted with PEI. The amino groups of PEI react with the carboxyl groups of the protected R7 to form amide derivatives. One example of a possible path of such reaction can be illustrated by reaction VII, which can be carried in the presence of the equimolar or greater amount of 1-ethyl-3(3-dimethylaminopropyl)carbodiimide, (EDC), having the formula $CH_3—CH_2—N=C=N—CH_2—CH_2—CH_2—N(CH_3)_2$. EDC is manufactured by Pierce Corp. of Rockford, Ill.

(VII)

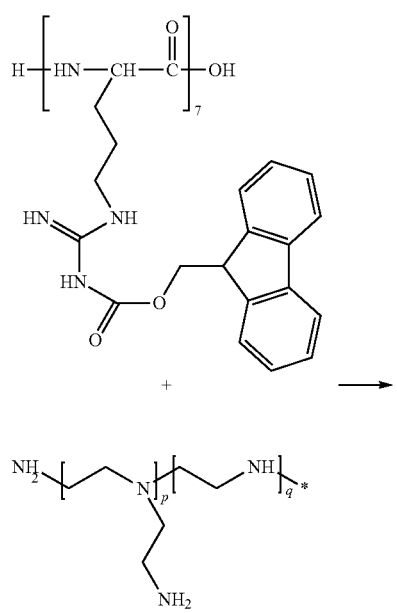

-continued

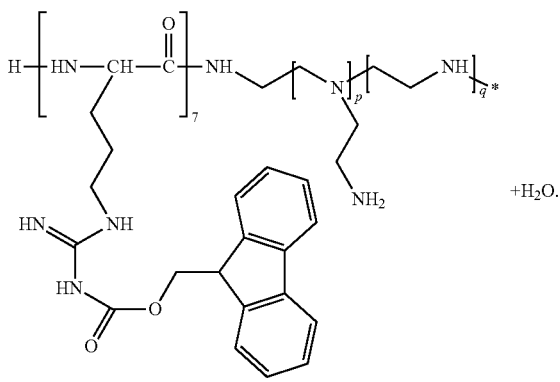

+H$_2$O.

Finally, the product of reaction (VII) is cleaved by 50% morpholine or other appropriate amine. As a result, the 9-fluorenylmethyl group is removed and R7 is tethered to PEI by the amide bond, as shown by the formula (VIII):

(VIII)

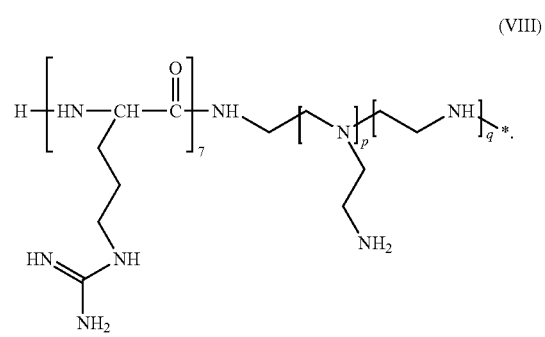

The reactions described above are conducted under the standard conditions which are known to those having ordinary skill in the art.

Again, the PEI-R7 conjugate of formula VIII is a POL-R7$^+$ cation (where POL is PEI). This cation can be brought in contact with one of the anionic polysaccharides described above, or a blend thereof, for example, Hep$^-$. As a result, R7 is entrapped on the stent surface by forming a complex POL-R7$^+$/Hep$^-$ as shown by reaction (VI).

According to yet another embodiment, R7 can be grafted to a surface containing carboxyl groups, for example, when the outermost layer of the stent coating includes PEAA. PEAA can react with unprotected R7, where carboxyl groups of PEAA and amino groups of R7 form an amide. One possible path of reaction, which is carried out in the presence of EDC or DCC, can be illustrated by reaction (IX):

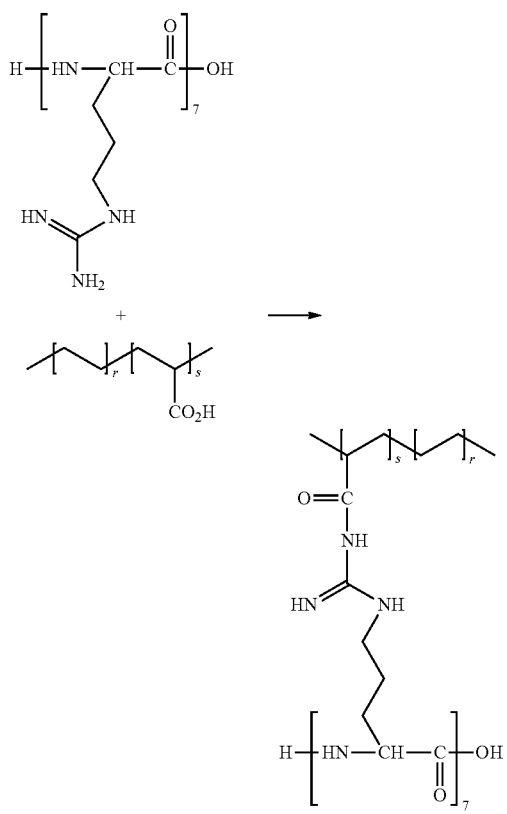

(IX)

Those having ordinary skill in the art will select the conditions suitable for carrying out reaction (IX), such as protecting amino groups R7 with FMOC and ultimately de-protecting these groups. The PEAA-R7 conjugate which is a product of reaction (IX) is a POL-R7$^+$ cation (POL being PEAA). This cation can be brought in contact with one of the anionic polysaccharides described above, or a blend thereof, for example, Hep$^-$. As a result, R7 is entrapped on the stent surface by forming a complex POL-R7$^+$/Hep$^-$ as shown by reaction (VI).

Alternatively, instead of using the surface containing the carboxyl groups, R7 can be grafted to the surface containing anhydride groups. Those having ordinary skill in the art will realize that the chemistry of R7-anhydride grafting would be similar to the reaction (IX), and will choose the appropriate conditions for accomplishing such grafting.

2. Ionic Coordination of R7.

Instead of covalently bonding R7 to carboxyl-containing polymers present in the outermost layer of the stent coating, R7 can be entrapped by forming an ionic complex with the carboxylated stent surface. The carboxyl groups are provided by acid-type polymers forming the stent coating, for example by PEAA.

Even R7 having its carboxyl group intact carries some positive charge and is cationic. It can be blended with PEAA and the pH of the blend can be raised by adding some base such as KOH. Under such alkaline conditions, PEAA will be ionized by de-protonization and will become anionic. Schematically, this can be illustrated by reaction (X):

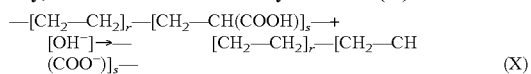

The anion (X) can be brought into contact with R7 causing coordination of the anion around R7. Such process has to be carried out under mild conditions so as to avoid the formation of the amide demonstrated by reaction (IX).

The product of ionic coordination of anion X around R7 will still be somewhat cationic because the positive charge on R7 is expected to be only partially offset by the negative charge on anion (X). Thus, the product of ionic coordination will be POL-R7$^+$ cation (POL being PEAA). This cation can be brought in contact with one of the anionic polysaccharides described above, or a blend thereof, for instance, Hep$^-$. As a result, R7 is entrapped on the stent surface by forming a complex POL-R7$^+$/Hep$^-$ as shown by reaction (VI), and the final coating will contain both anti-thrombotic and anti-restenotic components.

A variation of this method would allow entrapment of R7 on a coated stent where the coating is polyanionic. One way of creating a polyanionic coating is to include in the outermost layer of the coating an anionic polysaccharide, an anionic hydrogel or a mixture thereof, for example, heparin, hyaluronic acid, sulfated poly(ethylene glycol), sulfonated poly(ethylene glycol), carboxylated poly(ethylene glycol), or a mixture of anionic polysaccharides and hydrogels. Heparin can be applied onto the stent by techniques known to those having ordinary skill in the art. For example, a stent having a CARMEDA heparin coating or a TRILLIUM heparin coating can be used. Stents coated with CARMEDA or TRILLIUM coatings are manufactured by Cordis Corp., a Johnson & Johnson company of Miami Lakes, Fla., and BioInteractions, Ltd. of Reading, England, respectively.

The process of incorporating R7 on a heparin-coated stent can be demonstrated by the following example. Stainless steel coupons were coated with the BioInteractions' heparin TRILLIUM coating. The coupon was cut into about 1 cm width and about 3 cm length and weighed. The total heparin coated surface area was about 6 cm. About 0.1 gram of R7 was dissolved in about 1 gram of a 1:1 by weight water/acetone mixture. The coupon was immersed into R7 solution at 37° C. for about 1.5 hrs and dried at 65° C. for about 1 hr. Average loading for two coupons was about 330 μg/cm$^2$. The release rate was studied in PBS buffer (PH=7.4) at 37° C.

R7 content was semi-quantified with Bradford dye assay, which is commonly used to determine the total concentration of the peptide in the solution. The procedure is based on the formation of a complex between the dye and the peptide in the solution. The dye-peptide complex causes a shift in the wavelength at which the absorption of the dye reaches maximum from about 485 to 595 nm. The amount of peptide in the complex is proportional to the total peptide present.

A UV spectrometer (Cary 3E) was used in the experiment. R7 concentration was quantified by comparison with standard R7 curve. Within first 30 minutes, 80% of R7 eluted into the media, the remaining 22% continued eluting for 3 days.

According to another embodiment, the heparin-coated stent can be placed at a diseased site in a blood vessel in the usual manner. Due to the anionic nature of heparin, the stent coating will carry a negative charge. R7 is then administered systemically, for example, intravenously or orally. R7 will be carried through the circulatory system and when R7 approaches the stent, some of positively charged R7 will coordinate around heparin to form a R7$^+$/Hep$^+$ complex, thus trapping R7. After untrapped R7 is cleared from the circulatory system, trapped R7 will still persist for some time.

3. "Reversed" Covalent Conjugation.

According to this method, the order of steps discussed in the method of covalent conjugation above is reversed. In one embodiment, a polysaccharide such as heparin can be grafted to a surface containing amino groups, for example, when the outermost layer of the stent coating includes PEI. To graft, PEI is reacted with heparin utilizing amino groups of PEI and carboxyl groups of heparin. An amide bond is formed as in reaction VII, except that here instead of carboxyl groups of R7, carboxyl groups of heparin take part in the formation of the amide. As a result, the POL-Hep$^-$ anion is obtained, where POL is PEI and POL is covalently bonded to Hep$^-$ via the amide bond.

This POL-Hep$^-$ anion can be brought in contact with R7. As a result, R7 is entrapped on the stent surface by forming a complex POL-Hep$^-$/R7$^+$. It should be noted that the POL-Hep$^-$/R7$^+$ complex is a mirror image of the complex shown by reaction VI, where the positions of Hep$^-$ and R7$^+$ are reversed.

Alternatively, PEI can be reacted with a heparin derivative terminated with an aldehyde group, —C(O)H. Such reaction, conducted under the conditions to be selected by those having ordinary skill in the art will produce the same POL-Hep$^-$ product. Yet another alternative is to use in the outermost layer of the stent coating the polymer having aldehyde groups instead of PEI. The aldehyde groups will react with amino groups of heparin to yield the same POL-Hep$^-$ product. An amino-derivative of heparin R7 can also be used as a source of amino groups to be reacted with the aldehyde groups. Heparin products having aldehyde or amino moieties can be obtained from Celsus Laboratories, Inc. of Cincinnati, Ohio. The POL-Hep$^-$ product can be brought into contact with POL-Hep$^-$ to form the same POL-Hep$^-$/R7$^+$ complex as described above.

C. Incorporating PArg Into Stent Coatings Through the Use of Ion Exchange Microspheres In order to incorporate PArg into a stent coating, ion exchange microspheres can be fabricated, followed by absorbing PArg into the microspheres and by embedding the microspheres into the polymer of the reservoir coating layer and/or a topcoat layer.

Ion exchange microspheres or beads can be fabricated by suspension polymerization. For example, styrene and divinyl benzene can be co-polymerized in a suspension containing mineral oil, sodium polyacrylates as a dispersant and in the presence of a peroxide initiator of radical polymerization. In addition, ion exchange microspheres or beads can be fabricated by emulsion polymerization of at least one neutral monomer, at least one anionic monomer or at least one cross-linking monomer. The ionic functionality can be also added after the microsphere is formed.

Examples of neutral monomers that can be used in the process of synthesis of the microspheres by suspension or emulsion polymerization include acrylic or vinyl monomers, such as acrylamide $CH_2$=CH—$CONH_2$, methyl methacrylate $CH_2$=C($CH_3$)—$COOCH_3$, ethyl methacrylate $CH_2$=C($CH_3$)—$COOCH_2CH_3$, butyl methacrylate $CH_2$=C($CH_3$)$COOC_4H_9$, 2-hydroxyethyl methacrylate $CH_2$=C($CH_3$)—$COOCH_2$—$CH_2OH$, styrene $C_6H_5$—CH=$CH_2$, and PEG terminated on one terminus with either an acrylate or a methacrylate group (PEG-acrylate and PEG-methacrylate, respectively).

Examples of anionic monomers that can be used include acrylic or vinyl monomers having acid moieties, e.g., acrylic acid $CH_2$=CH—COOH, methacrylic acid $CH_2$=C($CH_3$)—COOH, ethyl acrylic acid $CH_2$=C($C_2H_5$)—COOH, propyl acrylic acid $CH_2$=C($C_3H_7$)—COOH, and carboxylated or sulfonated styrenes.

Examples of cross-linking monomers that can be used include acrylic or vinyl compounds, for example, propyleneglycol dimethacrylate ($CH_2$=CH—COO—CH($CH_3$)—$CH_2$—OOC—CH=$CH_2$), divinyl benzene ($CH_2$=CH—$C_6H_4$—CH=$CH_2$), N,N'-methylenebisacrylamide ($CH_2$=CH—CO—NH)$_2CH_2$, trimethylolpropane triacrylate ($CH_2$=CH—COOC)$_3$C—$CH_2$—), propyleneglycol diacrylate ($CH_2$=CH—COO—CH($CH_3$—$CH_2$—OOC—CH=$CH_2$), and PEG terminated on each terminus with either an acrylate or a methacrylate group (PEG-diacrylate and PEG-dimethacrylate, respectively).

The reaction of emulsion copolymerization is carried out in the presence of a typical initiator of radical polymerization such as benzophenone, hydroxycyclohexyl phenyl ketone, a blend of ammonium persulfate with N,N,N',N'-tetramethylethylenediamine, benzoyl peroxide or cumyl peroxide. The organic phase is selected from one or more of mineral oil, cyclohexane, cycloheptane, cyclooctane, octane, heptane, hexane, methylene chloride, chloroform or decalin. Those having ordinary skill in the art will select appropriate conditions under which the process of emulsion copolymerization is carried as well as a suitable emulsifier, for example one of TWEEN, SPAN, BRIJ, MYRJ, PLURONIC, TETRONIC or IGEPAL families.

TWEEN is a trade name of a family of polyoxyethelene-sorbitan monooleates. SPAN is a trade name of a family of sorbitan monostearates. BRIJ is a trade name of a family of polyoxyethylene ethers. TWEEN, SPAN, BRIJ are available from ICI Americas, Inc. of Bridgewater, N.J. MYRJ is a trade name of a family of propylene glycol monostearates and is available from Uniqema Corp. of New Castle, Del. PLURONIC is a trade name of poly(ethylene oxide-co-propylene oxide). TETRONIC is a trade name of a family of nonionic tetrafunctional block-copolymer surfactants. PLURONIC and TETRONIC are available from BASF Corp. of Parsippany, N.J. IGEPAL is a trade name of a family of amphoteric ethers and is available from Rhone-Poulenc, Inc. of Cranbury, N.J.

The microspheres which are a product copolymerization can have a diameter within a range of between about 0.2 and 10 micrometers. For example, microspheres having diameter between about 0.1 and 5 micrometers can be used. Following the fabrication of the microspheres, PArg such as R7, can be incorporated into the microspheres.

Furthermore, commercially manufactured microspheres, for example, microspheres made of a copolymer of styrene and divinyl benzene, can be used for incorporating PArg. Commercially manufactured microspheres are available from Advanced Polymer Systems, Inc. of Redwood City, Calif. or from Dow Chemical Co. of Midland, Mich.

The methods of incorporating R7 into the microspheres to form a microsphere-R7 complex may vary depending on the form of R7 used. For example, if R7 is in a free base form, R7 can be blended with the microspheres in the free acid form. Since the microspheres are porous, they will swell upon exposure to water and R7 in the free base form will be absorbed into the microspheres. If R7 already has counter-ions (e.g., acetate or trifluoroacetate anions) coordinated around R7, the microspheres can be mixed with R7 in aqueous solution followed by the process of dialysis described above. Alternatively, the microspheres can be first neutralized to the sodium salt, then placed into a column similar to a chromatographic column. An excess amount of R7$^+$/AN$^-$, for example, R7$^+$/Cl$^-$ can then be passed through the column causing the exchange process and trapping R7 inside the microspheres.

The microspheres loaded with R7 can optionally be dried and then mixed with a polymer solution which is used to fabricate the coating layer, e.g., the reservoir layer and/or a top coat layer. When the microspheres contact the organic solvent of the polymer solution, for example, dimethylacetamide, the water will be extracted from the microspheres causing their collapse, but R7 will remain incorporated into the polymer. The microspheres can also be first dehydrated with ethanol or lyophilized.

D. Incorporating PArg Into Stent Coatings Through the Use of Hydrogels

In order to incorporate PArg such as R7 into a stent coating, a hydrogel coating can be fabricated, followed by absorbing R7 into the hydrogel coating. After R7 has been absorbed, a topcoat layer can be optionally applied. If desired, this method can be used also for other polycationic peptides described above, and for any cationic therapeutically active material.

A primer layer can be optionally applied on the stent. Examples of polymers suitable for the optional primer layer include EVAL, PEAA or poly(butylmethacrylate) (PBMA). Alternatively, the primer layer can be made of pyrolytic carbon coating having abstractable hydrogen (diamond-like coating having both $sp^2$ and $sp^3$ carbon atoms and applied by plasma-assisted chemical vapor deposition). One example of a suitable diamond-like carbon coating is DYLYN which can be obtained from ART, Inc. of Buffalo, N.Y.

A hydrophilic UV-curable anionic coating can be applied forming a hydrogel. As a general rule, the degree of hydrophilicity of a polymer is proportional to the value of the Hildebrand solubility parameter δ. Polymers that are very hydrophilic may have a high δ value. A polymer that is sufficiently hydrophilic for use in the hydrophilic UV-curable anionic coating of the present invention can have a solubility parameter higher than about 11 $(cal/cm^3)^{1/2}$.

droitan sulfate, and/or heparin can also be optionally added to the formulation of the hydrophilic UV-curable anionic coating.

The formulation may also optionally contain up to 10% photoinitiator, based on the total mass of the non-volatile compounds. Examples of suitable photoinitiators include benzophenone and/or hydroxycyclohexyl phenyl ketone. The volatile compounds of the formulation include water, lower alcohols, and/or ketones, or mixtures thereof. Optionally, co-solvents, such as dimethylformamide, dimethylsulfoxide, and/or dimethylacetamide can be also added.

The formulation described above can be applied by any acceptable method, such as spraying, and then can be dried and UV-cured. R7 can then be applied onto the cured hydrogel followed by application of an optional topcoat. Acceptable polymers that can be used for the fabrication of the topcoat include PBMA, EVAL, PEAA, poly(vinylidene fluoride) and derivatives thereof.

The process of fabrication of the hydrophilic UV-curable anionic coating forming a hydrogel can be illustrated by the following example. A primer layer was first formed. A 3% (by mass) solution of poly(butylmethacrylate) in a blend of solvents (xylene, acetone and TECHSPRAY) was applied in a series of 10-second passes, to deposit 10 μg of coating per spray pass on a 13-mm TETRA stent (available from Guidant Corporation). Between the spray passes, the stent was dried for about 10 seconds using flowing air with a temperature of about 60° C. Seven spray passes were applied to form a 70 μg primer layer, followed by baking the primer layer at about 70° C. for approximately two hours. The hydrogel formulation for making the drug-polymer layer was then prepared as shown in Table 1.

TABLE 1

A Formulation for Preparing a Hydrophilic UV-Curable Anionic Hydrogel-Forming Coating

| Component | Amount, grams | Comment |
| --- | --- | --- |
| 3% solution of PAA in butyl alcohol | 18.0 | Polymer |
| 3% solution of PAA in isopropyl alcohol | 8.7 | Polymer |
| Photomer 4158 | 0.4 | Cross-linking monomer available from Cognis Corp. of Cincinnati, Ohio |
| PEG-acrylate | 0.05 | Monomer available from Sigma-Aldrich Corp. of St. Louis, Missouri |
| Benzophenone | 0.02 | Photoinitiator available from Sigma-Aldrich Corp. of St. Louis, Missouri |
| Hydroxycyclohexyl phenyl ketone | 0.02 | Photoinitiator available from Sigma-Aldrich Corp. of St. Louis, Missouri |
| Methyl ethyl ketone | 15.0 | Solvent |
| n-Butanol | 18.0 | Solvent |
| i-Propanol | 12.6 | Solvent |

The hydrophilic UV-curable anionic coating can have solid contents, i.e., non-volatile compounds, of between about 0.2% and about 25% by weight. The non-volatile compounds can include acrylate, methacrylate, allyl or vinyl monomers and/or oligomers, some of which may have non-ionic hydrophilic groups, oligoacrylate groups to provide high cross-linking, and/or anionic groups.

The non-ionic hydrophilic groups can include PEG-acrylate groups, PEG-methacrylate groups, hydroxymethyl methacrylate groups, and/or acrylamido groups. The oligoacrylate groups may include trimethylolpropane triacrylate groups and/or bis-acrylamido groups. The anionic groups can include carboxylates, sulfates, and/or phosphates. Hydrophilic polymers such as PEG, poly(vinyl pyrrolidone), hyaluronic acid, carboxymethyl cellulose, dextran sulfate, chon- The formulation described above was sprayed onto the primer layer and dried in the same way as described for the primer layer. About 200 μg of dry coating was formed. The coating was then exposed to UV-radiation for curing. 12 mW medium pressure mercury UV-lamp was used and the time of exposure was about 5 minutes. As a result, the hydrophilic anionic hydrogel drug-polymer layer was formed.

R7 was dissolved in 50% (mass) aqueous ethanol to obtain about 1% mass concentration of R7. Ammonium hydroxide was added to the R7 solution and the pH of the solution was raised to about 10. The solution was then sprayed onto the cured hydrogel drug-polymer layer in a series of passes until about 200 μg of dry R7 was deposited. In view of high hydrophilicity of the drug-polymer layer, R7 was absorbed and the stent was then baked at 70° C. for two hours. Finally, the stent coating was completed by spraying a topcoat. PBMA was used as a polymer forming the topcoat and about 100 μg of dry PBMA was deposited.

E. Incorporating PArg Into Stent Coatings Through the Use of Polyelectrolytes Polyelectrolytes are molecules with multiple charged sites. The peptides described above, such as poly(L-arginine), poly (D-arginine), poly(D,L-arginine), poly(L-lysine), poly(D-lysine), poly(δ-guanidino-α-aminobutyric acid), racemic mixtures of poly(L-arginine) and poly(D-arginine), and chitosan are polycations because they carry multiple positively charged groups. If a polycation is brought into contact with a polyanion, they will bond via ionic bonding.

In order to incorporate PArg, such as R7, into a stent coating, the polyelectrolyte properties of R7 can be exploited. A polyelectrolyte, e.g., cationic R7, or a mixture of polycationic polyelectrolytes, can be applied onto the stent and optionally dried, then a polyanionic electrolyte, or a mixture of polyanionic polyelectrolytes, can be applied. Examples of suitable polyanionic electrolytes include oligonucleotides, RNA, chondroitan sulfate, dextran sulfate, heparin and its derivatives, hyaluronic acid, hyaluronates, carboxymethyl cellulose, poly(acrylic acid), poly(methacrylic acid), poly(ethyl acrylic acid), poly(propyl acrylic acid, PEAA, and poly(ethylene-co-methacrylic acid). In one embodiment, a process of applying alternating polyelectrolyte layers can be employed and repeated any suitable number of times.

For example, a stent can be coated with a layer of PEI. The thickness of the PEI layer can be between about 0.05 and about 2.0 micrometers. Polyamino compounds, for example, poly(allyl amine) can be used in the alternative. The stent is dried and an aqueous solution of an anionic polysaccharide, such as heparin, is applied, for example, by spraying, and optionally dried, to form a heparin layer having the thickness of between about 0.05 and about 2.0 micrometers. Heparin can be either in an acid form or in an ionized form.

A layer of a polycationic peptide can then be applied, for example, R7 or other peptide selected from those described above, to form a layer having the thickness of between about 0.05 and about 2.0 micrometers. R7 can be either in a free base form or in an ionized form.

Optionally, a binder material can be included in either or both polyelectrolyte coating solutions to modify mechanical, physical or pharmacological properties of the coating. Examples of suitable binder materials include poly(vinyl alcohol), EVAL, PVP, hydroxyethyl cellulose and cellulose acetate. Each polyelectrolyte can be in a 100% water solution, or, optionally, the solution can contain some water miscible co-solvents, such as dimethyl formamide, dimethyl acetoamide, dimethyl sulfoxide, acetone, and tetrahydrofurane.

The process of applying of alternating heparin and R7 layers is then repeated any suitable number of times, for example, between 2 and 100 times, until the desired thickness of the coating has been achieved. Alternatively, the polycationic polyelectrolyte forming the second and each successive layer can be one of the polycationic polyelectrolytes other than R7 as described above, or a mixture of such polycationic polyelectrolytes. Similarly, the polyanionic polyelectrolyte can be different polyanionic polyelectrolytes for each of the successive layers.

As a result of the above-described procedure, a multi-layer structure is built, where the layers of the polycationic and polyanionic polyelectrolytes alternate, and the layers of R7 and heparin interdiffuse and bind to one another. The binding can be ionic or, if R7 is in the free base form and heparin in the acid form, via acid-base neutralization. Upon exposure to blood, or other body fluids, both R7 and heparin will be slowly released from the stent's surface and will be carried to the diseased site in the body, providing enhanced therapeutic effect.

A variation of the polyelectrolyte method described above can be illustrated by the following example. The conventional EFD coater can be modified to have dual barrels. One barrel can contain R7 and EVAL dissolved in the mixture of about 30% by mass of methanol and about 70% by mass of dimethylacetamide. The other barrel can contain a solution of heparin in EVAL, the solution comprised of about 0.1 g of sodium heparin, about 1 ml of formamide, about 3 g of 5% EVAL in dimethylacetamide, and about 1 gram of methanol. A layer of R7/EVAL can be spray coated followed by spraying a layer of sodium heparin/EVAL. The procedure of applying alternating layers of R7/EVAL and sodium heparin/EVAL can be repeated until the desired coating weight is reached, for example, 600 μg for a 13 mm TETRA stent. Optionally, a topcoat of EVAL or PBMA polymer can be finally applied.

In accordance to one embodiment of the invention, a therapeutic substance or active agent can be incorporated into the described embodiments of the coating. The active agent could be for inhibiting the activity of vascular smooth muscle cells; more particularly the agent can be directed at inhibiting abnormal or inappropriate migration and/or proliferation of smooth muscle cells to inhibit restenosis. Generally speaking, the active agent can include any substance capable of exerting a therapeutic or prophylactic effect in the practice of the present invention. Examples of the drugs which are usable include antiproliferative substances such as actinomycin D, or derivatives and analogs thereof. Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, docetaxel, methotrexate, azathioprine, vincristine, vinblastine, fluorouracil, doxorubicin hydrochloride, and mitomycin. Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin. Examples of such cytostatic or antiproliferative agents include angiopeptin, angiotensin converting enzyme inhibitors such as captopril, cilazapril or lisinopril, calcium channel blockers (such as nifedipine), colchicine, fibroblast growth factor (FGF) antagonists, fish oil (ω-3-fatty acid), histamine antagonists, lovastatin (an inhibitor of HMG-CoA reductase, a cholesterol lowering drug), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin, estradiol, clobetasol, dexamethasone, and structural analogs or functional derivatives thereof.

The coatings and methods of the present invention have been described in conjunction with a stent. The stent can be used in any part of the vascular system, including neurological, carotid, coronary, renal, aortic, iliac, femoral or any other peripheral vascular site. The stent can be balloon-expandable or self-expandable. There are no limitations on the size of the stent, its length, diameter, strut thickness or pattern. The use of the coating is, however, not limited to stents and the coating can also be used with a variety of other medical devices. Examples of the implantable medical device that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE (Nitinol), tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof.

Devices made from bioabsorbable or biostable polymers can also be used with the embodiments of the present invention. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

We claim:

1. A coating for an implantable medical device, wherein the coating comprises a polymer and a complex comprising a polycationic peptide and a counter-ion, wherein the complex is bonded to the polymer.

2. The coating of claim 1, wherein the medical device comprises a stent.

3. The coating of claim 1, wherein the polymer comprises a component selected from a group consisting of hydroxyl, glycidyl, amino, carboxyl, or aldehyde functional groups, and a combination thereof.

4. The coating of claim 1, wherein the polymer comprises a component selected from a group consisting of poly(ethylene-co-vinyl alcohol), poly(butylmethacrylate-co-2-hydroxyethyl methacrylate), poly(butylmethacrylate-co-acrylic acid), poly(ethylene glycol), poly(ethylene-co-glycidyl methacrylate), poly(ethyleneimine), poly(ethylene-co-acrylic acid), and a combination thereof.

5. The coating of claim 1, wherein the polycationic peptide comprises a component selected from a group consisting of poly(L-arginine), poly(D-arginine), poly(D,L-arginine), poly(L-lysine), poly(D-lysine), poly(δ-guanidino-α-aminobutyric acid), mixtures of poly(L-arginine) and poly(D-arginine), chitosan, and a combination thereof.

6. The coating of claim 1, wherein the counter-ion comprises an anionic polysaccharide, an anionic hydrogel, or a combination thereof.

7. The coating of claim 6, wherein the anionic polysaccharide comprises a component selected from a group consisting of heparin, a heparin salt, a heparinoid, dermatan sulfate, keratan sulfate, chondroitin sulfate, hyaluronic acid, a hyaluronate, and a combination thereof.

8. The coating of claim 6, wherein the anionic hydrogel comprises a component selected from a group consisting of sulfated poly(ethylene glycol), sulfonated poly(ethylene glycol), carboxylated poly(ethylene glycol), and combinations thereof.

* * * * *